(12) United States Patent  
Martinsson (10) Patent No.: US 8,267,902 B2  
(45) Date of Patent: Sep. 18, 2012

(54) SYRINGE, CAPSULE DEVICE THEREFORE, AND SYRINGE DEVICE

(75) Inventor: Patrick Martinsson, Stockholm (SE)

(73) Assignee: Insulution Svenska AB, Stockholm (SE)

( * ) Notice: Subject to any disclaimer, the term of this patent is extended or adjusted under 35 U.S.C. 154(b) by 269 days.

(21) Appl. No.: 12/307,827

(22) PCT Filed: Jul. 5, 2007

(86) PCT No.: PCT/SE2007/050503  
§ 371 (c)(1), (2), (4) Date: Jan. 7, 2009

(87) PCT Pub. No.: WO2008/004976  
PCT Pub. Date: Jan. 10, 2008

(65) Prior Publication Data  
US 2009/0312714 A1    Dec. 17, 2009

(30) Foreign Application Priority Data  
Jul. 7, 2006    (SE) ...................................... 0601499

(51) Int. Cl.  
*A61M 5/315*    (2006.01)

(52) U.S. Cl. ........ 604/220; 604/192; 604/199; 604/263; 206/364

(58) Field of Classification Search ................. 604/187, 604/192, 197, 198, 199, 227, 263, 220, 218; 206/363, 364, 365, 571  
See application file for complete search history.

(56) References Cited

U.S. PATENT DOCUMENTS

| | | | |
|---|---|---|---|
| 764,564 A * | 7/1904 | Dreyer | ........................ 604/192 |
| 2,400,722 A | 5/1946 | Swan | |
| 2,473,733 A | 6/1949 | Smith | |
| 2,707,466 A | 5/1955 | Hoskins et al. | |
| 2,860,635 A | 11/1958 | Wilburn | |
| 3,272,322 A | 9/1966 | Ogle | |

(Continued)

FOREIGN PATENT DOCUMENTS

GB    1379509    1/1975

(Continued)

OTHER PUBLICATIONS

PCT/ISA/210—International Search Report—Oct. 5, 2007, (3 pages).

(Continued)

*Primary Examiner* — Bhisma Mehta  
(74) *Attorney, Agent, or Firm* — Venable LLP; Eric J. Franklin (57) ABSTRACT

A syringe including a front end and a rear end. A front portion of the syringe having an axially extending hollow needle that projects from the front end. The rear end of the needle is in fluid communication with a space that extends substantially to the rear end of the syringe. A plunger extends axially and is movable to and fro in the space and is designed such that, when drawn out, it sucks liquid through the needle and, when pressed in, discharges liquid through the needle. A radially projecting flange element in the front portion of the syringe is designed in such a way that it can be gripped between the thumb and middle finger of a user's hand. The syringe is dimensioned so as to permit injection using the index finger of the same hand. A capsule device for at least partially accommodating a syringe. A syringe device.

10 Claims, 4 Drawing Sheets

U.S. PATENT DOCUMENTS

| | | | |
|---|---|---|---|
| 3,878,846 A | | 4/1975 | Rimbaud |
| 3,930,499 A * | | 1/1976 | Rimbaud .................. 604/197 |
| 4,148,316 A | | 4/1979 | Xanthopoulos |
| 4,484,915 A | | 11/1984 | Tartaglia |
| 5,116,319 A | | 5/1992 | van den Haak |
| 5,417,326 A | | 5/1995 | Winer |
| 5,509,903 A * | | 4/1996 | Grendahl et al. .......... 604/187 |
| 5,997,514 A * | | 12/1999 | Balestracci ................ 604/227 |
| 6,283,946 B1 * | | 9/2001 | Fischer ...................... 604/218 |
| 2003/0132128 A1 * | | 7/2003 | Mazur ........................ 206/364 |
| 2004/0116875 A1 | | 6/2004 | Fischer et al. |

FOREIGN PATENT DOCUMENTS

| | | |
|---|---|---|
| GB | 2003037 A | 3/1979 |
| JP | 4876390 | 10/1973 |
| JP | 5452890 | 4/1979 |
| JP | 6334410 U | 3/1988 |
| JP | 3035665 U | 9/1997 |
| JP | 2000202026 A | 7/2000 |
| WO | WO-9822166 A1 | 5/1998 |
| WO | WO-2006018626 A1 | 2/2006 |

OTHER PUBLICATIONS

PCT/IPEA/409—International Preliminary Report on Patentability—Jun. 12, 2008, (8 pages).

European Search Report—issued in counterpart European application 07769049.3—May 3, 2011.

First Office Action—issued in counterpart Chinese patent application 200780032712.X—Apr. 13, 2011.

Notice of Reasons for Rejection issued in Japanese patent application 2009-519411—Feb. 2, 2012.

Office action issued by Chinese patent office in counterpart application 200780032712.X—Apr. 12, 2012.

* cited by examiner

SYRINGE, CAPSULE DEVICE THEREFORE, AND SYRINGE DEVICE

CROSS-REFERENCE TO RELATED APPLICATIONS

This application claims priority to Swedish patent application 0601499-7 filed 7 Jul. 2006 and is the national phase under 35 U.S.C. §371 of PCT/SE2007/050503 filed 5 Jul. 2007.

TECHNICAL FIELD

The invention relates to a syringe, especially an insulin syringe. The invention also relates to a capsule device, for at least partially accommodating a syringe. The invention further relates to a syringe device.

BACKGROUND

Many people suffer from diabetes. Because of their diabetes, many of these people have to inject several times a day, normally after taking food, and therefore need to carry insulin syringes around with them wherever they go. There are presently a number of different designs of insulin syringes of greater or lesser sophistication with which the dose, i.e. the number of units to be injected, can be set, and which accommodate insulin for several dosages.

A problem with such insulin syringes is that, although there are some models having the shape of a large pen or the like, they can in some circumstances be too awkward to carry around. In the summer, for example, when people wear fewer clothes, for example at the beach or the like, it is a problem always having to carry around a syringe shaped like a pen. Nor is it particularly convenient to carry it around in trouser pockets, as it can press against the skin, for example when sitting down or the like. This means that in such cases the insulin is not taken regularly, nor is it taken as often as may be required, thus increasing the risk of other diseases, for example liver diseases. Moreover, they do not always give an exact dose. Instead, the dose obtained may vary from a given metered dose quantity.

A more exact dose is provided by conventional syringes with an axially extending plunger that moves to and fro and is designed such that, when drawn out, it sucks liquid through the needle to the space and, when pressed in, discharges liquid from the space through the injection needle, but they are difficult to use on oneself and are also difficult to carry around on one's person.

OBJECT OF THE INVENTION

An object of the present invention is to make available a syringe which, while being relatively easy to dose, permits an exact dosage and is easy to use and carry around.

DISCLOSURE OF THE INVENTION

This object and others that will become evident from the following description are achieved by means of a syringe, a capsule device and a syringe device according to the above.

By means of a syringe with a front end and a rear end, the front portion of the syringe having an axially extending hollow needle that projects from the front end, the rear end of the needle being in fluid communication with a space that extends substantially to the rear end of the syringe, and the syringe comprising a plunger which extends axially and is movable to and fro in the space and is designed such that, when drawn out, it sucks liquid, for example insulin, through the needle and, when pressed in, discharges liquid through the needle, wherein a radially projecting flange element in the front portion of the syringe is designed in such a way that it can be gripped between the thumb and middle finger of a user's hand, the syringe being dimensioned such as to permit injection using the index finger of the same hand, a syringe is obtained which is very easy to use on oneself, for example for injecting insulin into the abdominal region. By virtue of the size of the syringe, which is relatively short, it is easier to carry it around on one's person. In this way it is easier to regularly inject insulin sufficiently often, even when at the beach or the like. This means that diseases, for example liver diseases, related to irregular use and/or to the insulin not being taken often enough are reduced, i.e. health problems associated with inadequate intake of insulin are reduced. Since the syringe is of a conventional type with a simple structure, it is possible to obtain an exact dose and to ensure simple dosage. Moreover, the flange element allows a protective casing to be engaged over the needle in order to protect the user when the syringe is not in use and to protect the needle, the flange element functioning as a limit stop. The flange element also allows a protective casing to be engaged over the rear end of the syringe when the plunger is drawn out, the flange element functioning as a limit stop in such a way that the plunger is prevented from being pressed in, which means that the syringe can be charged in advance and then carried around in order to be used as and when required.

The flange element preferably has a substantially oval cross section. This improves the grip on the flange element between the thumb and the middle finger.

The flange element preferably has a substantially circular cross section. This provides a good grip and allows the syringe to be gripped at all angles, regardless of how the syringe is turned. The simple geometry also simplifies production.

The flange element preferably comprises at least two circumferential flange portions arranged substantially parallel to one another, which improves the grip on the flange element between the thumb and middle finger.

The flange element is preferably flexible, which improves the grip and provides increased comfort.

The syringe preferably comprises means for releasably securing a sleeve element, said means being arranged on at least one of the front portion and rear portion of the syringe.

The syringe, with the plunger drawn out, preferably has a length in the range of 30-80 mm, preferably 40-60 mm. An advantage of the syringe being short is that it is much easier to carry around. A further advantage of the size of the syringe is that it is easier to use compared to a conventional longer syringe, since handling is simplified.

By means of a capsule device designed to at least partially accommodate at least one syringe according to any of the embodiments according to the invention above, comprising at least one rear sleeve element that is dimensioned such that, when the plunger of the respective syringe is drawn out, it will cover the extended protruding plunger of the respective syringe in such a way that, when the sleeve element is engaged over the plunger, the plunger cannot be pressed in, the syringe can be kept pre-dosed such that it is ready to be used when a user requires it. This also makes it easier to carry the syringe around, i.e. there is no risk of the user pressing the plunger and of insulin or the like being accidentally discharged while carrying the syringe around.

The capsule device preferably further comprises at least one front sleeve element designed to cover the needle of a respective syringe when the syringe is not in use. This makes it possible to protect the syringe in such a way that the needle cannot be damaged or a person cannot accidentally sustain an injury from the needle. This also makes it easier to carry the needle around, i.e. there is no risk of the user being injured by the needle while carrying the syringe around.

The front flange portion of the flange element of the syringe is preferably designed such that, upon engagement of the front sleeve element, it acts as a limit stop for the front sleeve element. This prevents the needle from being damaged and avoids a person being injured by the needle.

The rear flange portion of the flange element of the syringe is preferably designed such that, upon engagement of the rear sleeve element, it acts as a limit stop for the rear sleeve element. This avoids the plunger being inadvertently pressed in and liquid, i.e. insulin, being discharged when not required, i.e. when the syringe is not intended to be used. This is also a reliable way of keeping the syringe pre-dosed.

A further advantage of using the flange element as a limit stop for the front sleeve element and rear sleeve element is that the capsule device takes up less space than if the whole syringe were to be enclosed.

Means are preferably provided for releasably securing at least one of front sleeve element and rear sleeve element. This permits simple handling, when the sleeve elements remain in place protecting the syringe, until a user removes them, i.e. the risk of them inadvertently coming loose is minimized.

Preferably, at least one of front sleeve element and rear sleeve element comprises a fastening means, for example a fastening eyelet, for attachment of a key ring or the like. In this way, the syringe/syringes can be carried on a key ring, on a strap round the neck, or such like, thus making it easier to carry the syringe around on one's person.

Preferably, at least two rear sleeve elements are connected in parallel to one another to form a rear capsule part. In this way, several syringes can be carried around in one and the same capsule device, in which case it is possible for different syringes to be differently pre-dosed. The capsule device can be designed here like a small cigarette case or the like, which means that the capsule device can easily be carried in a shirt pocket, trouser pocket, jacket pocket or the like.

Means are preferably provided for liquid-tight enclosure of the syringe by the sleeve elements. In this way, the syringe can be carried in the capsule device without risk of exposure to liquid from outside, for example water. The syringe can consequently be carried around when bathing, for example.

DESCRIPTION OF THE FIGURES

The present invention will be better understood by referring to the following detailed description read in conjunction with the attached drawings, in which identical reference numbers designate identical parts depicted in the many views, and in which.

DETAILED DESCRIPTION OF THE INVENTION

Figure 1:
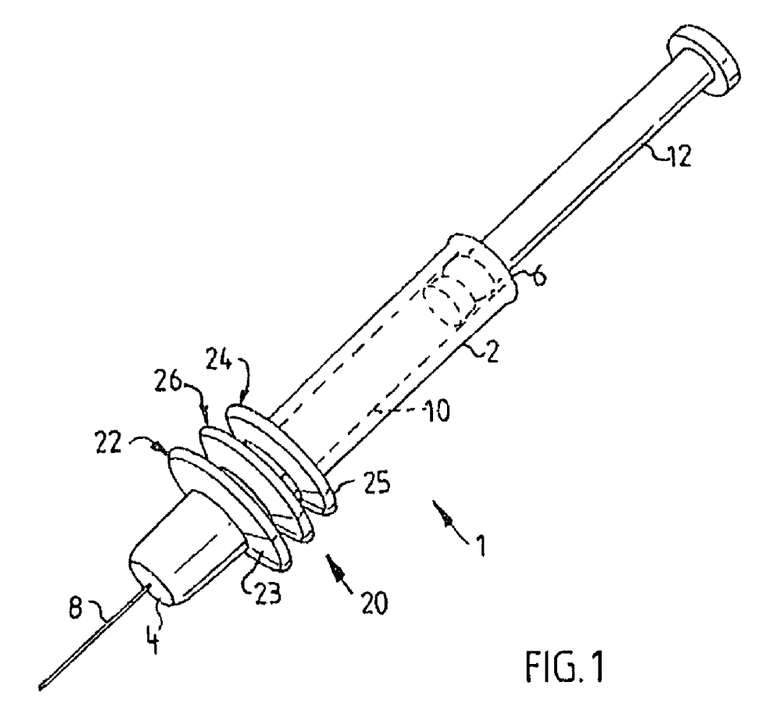
FIG. 1 shows a schematic perspective view of a syringe according to a first embodiment of the present invention.

FIG. 1 shows a perspective view of a syringe 1 according to the invention, having a substantially cylindrical body 2 with a front end 4 and a rear end 6. In its front portion, the syringe has an axially extending hollow needle 8, which projects from the front end 4. The rear end of the needle is in fluid communication with a space 10 that extends substantially to the rear end 6 of the body. The syringe also comprises a plunger or piston rod 12 which extends axially and moves to and fro in the space 10, where the plunger 12 comprises a piston arranged in the space 10 and the piston rod extends axially from the piston and out of the rear end of the syringe, and which plunger 12 is designed such that, when drawn out, it sucks liquid, i.e. insulin, through the needle 8 to the space 10 and, when pressed in, discharges liquid from the space 10 through the needle 8 for injection. The space 10 in the syringe is preferably transparent. The plunger preferably has graduations in the form of markings on its outside, for example lines and/or numerals. Alternatively, the space in the syringe has graduations in the form of markings, for example lines and/or numerals, indicating dose units and arranged axially along the space. This allows the user to easily meter the desired number of dose units.

In its front portion, the body 2 of the syringe 1 has a radially protruding forward flange element 20 or grip element. The flange element 20 has, in one embodiment, a substantially oval cross section. According to another embodiment, the flange element 20 has a circular cross section. Alternative cross sections of the flange element are conceivable, such as rectangular, square, waist-shaped, etc. The flange element 20 has a front flange portion 22 with a surface 23 facing in the direction of the front end of the syringe 1, and a rear flange portion 24 with a surface 25 facing in the direction of the rear end of the syringe. The flange element preferably also comprises a middle flange portion 26 arranged between the front flange portion 22 and the rear flange portion 24. The flange portions 22, 24, 26 are preferably arranged parallel to one another. The front flange portion 22 preferably has a greater cross-sectional diameter, i.e. a greater radial extension, than the middle flange portion 26, and the middle flange portion 26 preferably has a greater cross-sectional diameter, i.e. a greater radial extension, than the rear flange portion 24. This further improves the grip around the flange element 20 and minimizes the risk of the user letting it slip during injection. The flange element 20 is designed in such a way that it can be gripped between the thumb and middle finger, and it accordingly has an extent in the axial direction. The extent in the axial direction is preferably such that the surface of the flange element 20 can be gripped between the thumb and middle finger, as described above. The flange element 20 is preferably flexible and is made of a suitable material such as polypropylene or rubber of suitable hardness and friction, such that the grip between the thumb and middle finger is optimized.

The syringe 1 is dimensioned in such a way that, when the plunger 12 is drawn out during use, the user, holding the syringe 1 with the thumb and middle finger of one hand on the flange element 20, can easily carry out an injection by pressing the plunger with the index finger of the same hand, such that insulin is injected, for example into the abdominal region. With the plunger drawn out, the syringe preferably has a length in the range of 30-80 mm, preferably 40-60 mm.

Figure 1A:
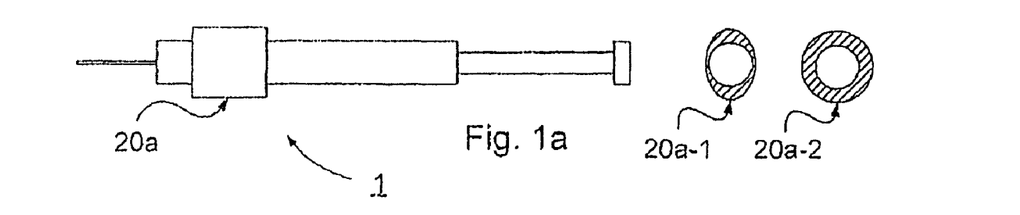
FIGS. 1a-f show schematic side views and cross-sectional views of the syringe according to alternative embodiments of the present invention.
Figure 1B:
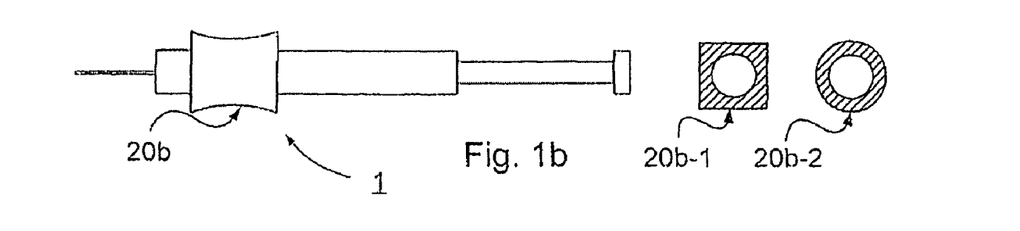
Figure 1C:
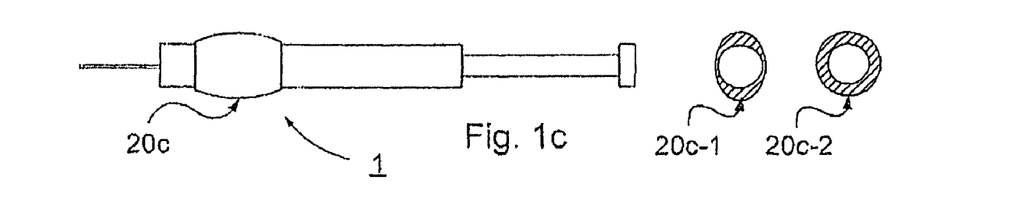
Figure 1D:
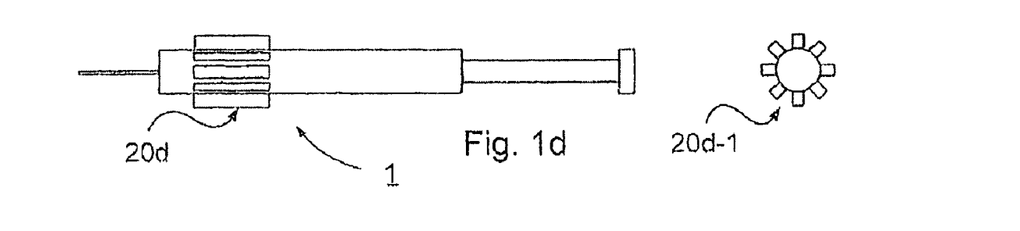
Figure 1E:
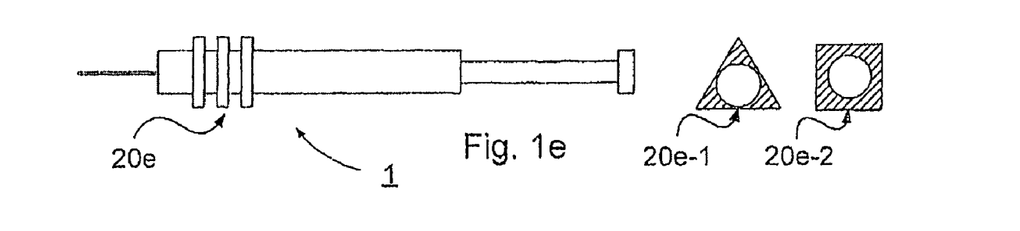
Figure 1F:
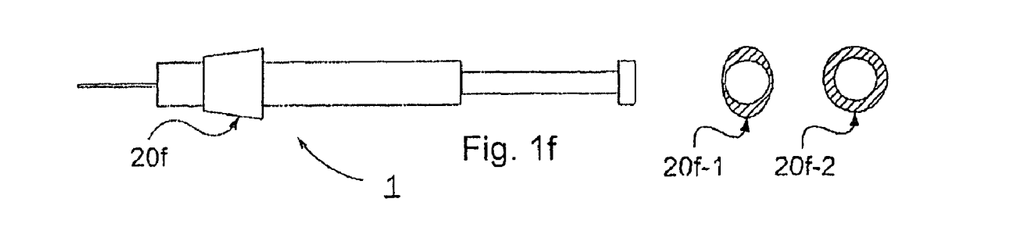

FIGS. 1a-f show schematic side views and cross-sectional views of the syringe 1 according to alternative embodiments of the flange element 20a-20f or grip element 20a-20f of the present invention, where the flange element 20a-20f has an axial extent and a radial extent. FIG. 1a shows a side view of the syringe 1 in which the flange element 20a has a cylindrical shape and, according to a first variant 20a-1, an oval cross section, and, according to a second variant, a circular cross section 20a-2. Alternative cross sections are also conceivable, such as square, rectangular, pentagonal, triangular, etc. FIG. 1b shows a side view of the syringe 1 in which the flange element 20b has a waist-shaped profile, i.e. a substantially cylindrical shape where the cross-sectional width decreases towards the axial centre of the cylinder, and, according to a first variant 20b-1, a square cross section, and, according to a second variant, a circular cross section 20b-2. Alternative cross sections are also conceivable, such as rectangular or oval or the like. FIG. 1c shows a side view of the syringe 1 in which the flange element 20c has a bulging profile, i.e. a substantially cylindrical shape where the cross-sectional width increases towards the axial centre of the cylinder, and, according to a first variant 20c-1, an oval cross section, and, according to a second variant, a circular cross section 20c-2. Alternative cross sections are also conceivable. FIG. 1d shows a side view of the syringe 1 in which the flange element 20d has axially extending flange portions preferably uniformly distributed and extending radially out from the body of the syringe 1 in accordance with the cross section 20d-1. FIG. 1e shows a side view of the syringe 1 in which the flange element 20e has radially extending, circumferential flange portions, and, according to a first variant 20e-1, a triangular cross section, and, according to a second variant, a square cross section 20e-2. Alternative cross sections are also conceivable. FIG. 1f shows a side view of the syringe 1 in which the flange element 20f has a trapezoid profile decreasing in width towards the front part of the syringe, and, according to a first variant 20f-1, an oval cross section, and, according to a second variant, a circular cross section 20f-2. Alternative cross sections are also conceivable. The syringe 1 with the alternative embodiments of the flange element 20a-20f otherwise has the same function as the embodiment with the flange element described under FIG. 1. The flange element 20a-20f according to the embodiments above is preferably flexible and made of a suitable material such as polypropylene or rubber of suitable hardness and friction, such that the grip between the thumb and middle finger is optimized. The surfaces of the flange element 20a-20f can be grooved, raised, have knobs/points and so on, in order to optimize the grip.

Figure 2:
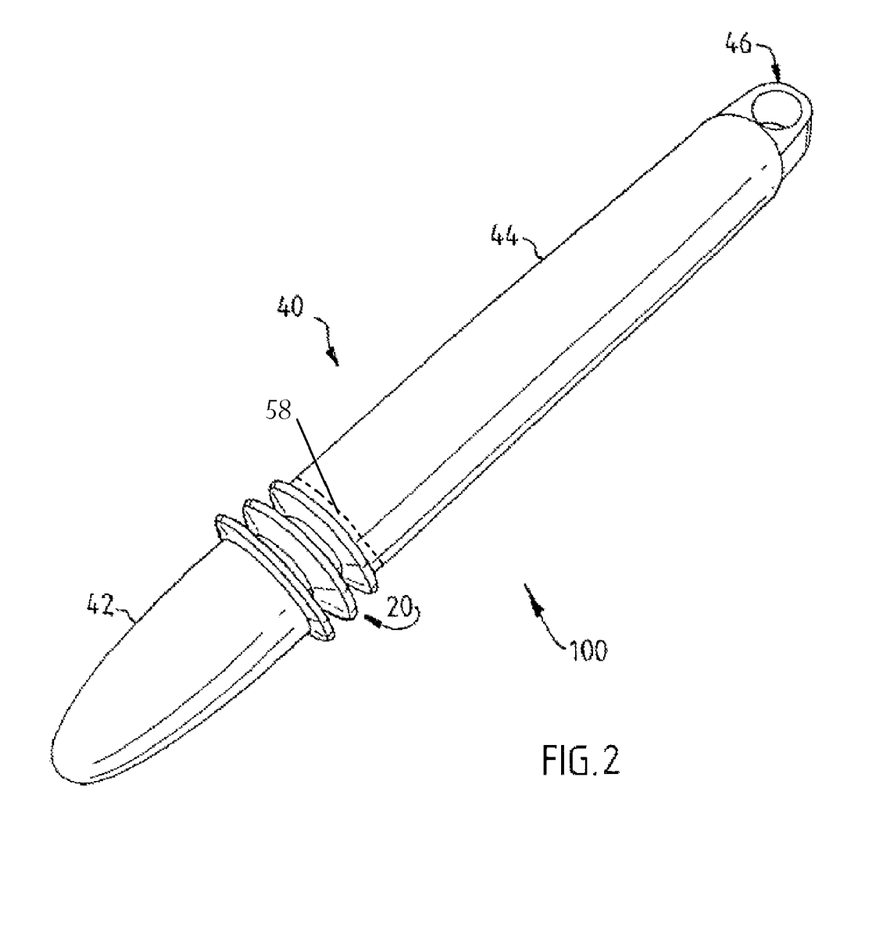
FIG. 2 shows a schematic perspective view of a syringe device according to a first embodiment of the invention, comprising a capsule device according to a first embodiment of the invention.

FIG. 2 shows a perspective view of a syringe device 100 according to a first embodiment of the invention, comprising a capsule device 40 according to a first embodiment of the invention and the syringe 1 according to the invention, which capsule device 40 is designed to at least partially cover the syringe 1. The capsule device 40 comprises a front sleeve element 42 designed to cover the needle 8 when the syringe 1 is not in use, the front flange portion 22 of the flange element 20 being designed as a limit stop for the front sleeve element 42, which sleeve element 42 is preferably designed to be secured releasably by retention means 28. The retention means can, for example, be a snap-fit arrangement or a thread arrangement, i.e. external threads on the syringe 1 and internal threads on the front sleeve element 42 adapted such that they can be screwed together. The retention means can be arranged on one of the front portion and a rear portion of the syringe. The front sleeve element 42 therefore functions as a protective casing to prevent damage to the needle 8 when the syringe 1 is not in use.

The capsule device 40 additionally comprises a rear sleeve element 44, which is dimensioned such that, when the plunger 12 is drawn out, i.e. when dosing has taken place, it covers the protruding plunger 12, and the rear flange portion 24 of the flange element 20 is in this case designed as a limit stop for the rear sleeve element 44, which in turn means that the drawn-out plunger 12, when the rear sleeve element 44 is engaged, cannot accidentally be pressed in and discharge insulin. The rear sleeve element 44 is preferably secured releasably by retention means. The retention means can, for example, be a snap-fit arrangement or a thread arrangement, i.e. external threads on the syringe and internal threads on the rear sleeve element adapted such that they can be screwed together. In FIG. 2, a syringe is housed in the capsule device, as is evident from the flange element 20 of the syringe between the front sleeve element 42 and the rear sleeve element 44. The capsule device 40 can be correspondingly connected to the syringe 1 with the alternative embodiments of the flange element 20a-20f.

The capsule device further comprises a fastening means 46, designed in the figure as a recess 46 or fastening eyelet 46, arranged at the rear end of the rear sleeve element. Alternatively, the fastening means could be arranged at the end of the front sleeve element, or at both ends. The retention means is preferably arranged such that, when the respective sleeve element 42, 44 is engaged on the syringe, a liquid-tight closure is obtained, for example by sealing means 58. The means for obtaining the liquid-tight closure when the syringe is housed in the capsule device can also be separate from the retention means and can, for example, be a sealing ring, or can involve the syringe being cone shaped or the like. The capsule device is preferably made of a durable material.

Figure 3:
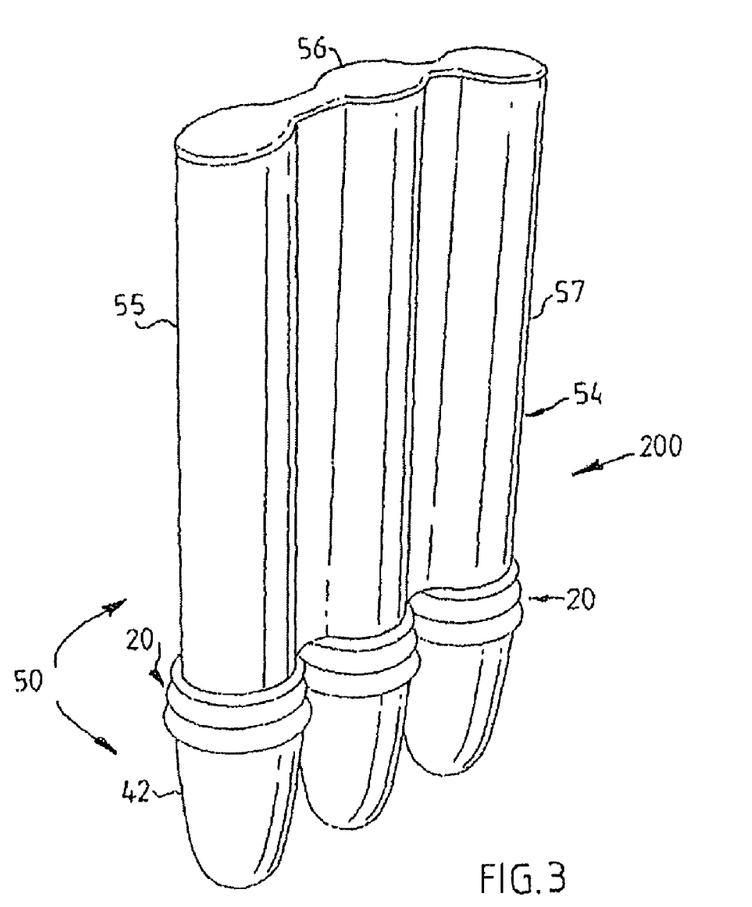
FIG. 3 shows a schematic view of a syringe device according to a second embodiment of the invention comprising a capsule device according to a second embodiment of the invention.

FIG. 3 shows a perspective view of a syringe device 200 according to a second embodiment of the invention, comprising a capsule device 50 according to an alternative embodiment of the invention, which capsule device 50 is designed to at least partially accommodate three syringes. The capsule device comprises a front sleeve element 42 for each syringe 1, designed to cover the needle 8 of each syringe 1 when the syringe is not in use, the front flange portion 22 of the flange element 20 of each syringe being designed as a limit stop for the respective sleeve element 42, which sleeve element 42 is preferably designed to be secured releasably by retention means. The retention means can, for example, be a snap-fit arrangement or a thread arrangement, i.e. external threads on the syringe 1 and internal threads on the front sleeve element 42 adapted such that they can be screwed together.

The capsule device 50 additionally comprises a rear capsule part 54 comprising three interconnected and mutually parallel rear sleeve elements 55, 56, 57 which are arranged in a row and constitute portions of the rear capsule part. The sleeve elements 55, 56, 57 are accordingly arranged in such a way that, in cross section of the rear capsule part 54, an imaginary line drawn from the centre of each sleeve element 55, 56, 57 forms a straight line. The sleeve elements 55, 56, 57 are dimensioned such that, when the plunger 12 is drawn out, i.e. when dosing has taken place, they are intended to cover the protruding plunger 12 of the respective syringe 1, and the rear flange portion 24 of the flange element 20 of each syringe 1 is designed as a limit stop for the respective sleeve element 55, 56, 57 of the rear capsule part 54, which in turn means that the drawn-out plunger 12, when the respective sleeve element 55, 56, 57 is engaged on the respective syringe 1, cannot be accidentally pressed in and discharge insulin. The rear capsule part 54 is preferably secured releasably by retention means. The retention means can, for example, be a snap-fit arrangement. In FIG. 3, three syringes are accommodated in the capsule device 50, one in each front and rear sleeve element respectively. The capsule device 50 can be correspondingly connected to the syringe 1 with the alternative embodiments of the flange element 20a-20f.

As in the first embodiment according to FIG. 2, the capsule device should comprise a securing means (not shown), designed as a recess or fastening eyelet, for example, and arranged at the rear end of the rear sleeve element, or at the end of the front sleeve element, or at both ends. The retention means is preferably designed such that, when the respective sleeve element 42, 55, 56, 57 is engaged on the syringe, a liquid-tight closure is obtained, for example by sealing means. The means for obtaining the leaktight closure when the syringes are housed in the capsule device can also be separate from the retention means and can, for example, be a sealing ring, or can involve the syringes being cone shaped or the like. The capsule device is preferably made of a durable material.

Alternatively, the rear capsule part 54 comprises, instead of three sleeve elements, a number greater than three, for example four or five, or fewer than three, i.e. two sleeve elements. The sleeve elements of the rear capsule part are alternatively arranged parallel to one another such that, in a cross section of the rear capsule part, an imaginary line drawn from the centre of the respective sleeve element forms a triangle (in the case of three sleeve elements), a square (in the case of four sleeve elements), etc. Other geometries are also conceivable.

Alternatively, the capsule device can be designed such that it completely covers at least one syringe, in which case the front sleeve element and the rear sleeve element are designed to be releasably secured to one another by retention means, i.e. they are connected directly to one another instead of being connected via the flange element and/or the retention means of the syringe/flange element. The retention means can, for example, be a snap-fit arrangement, or a thread arrangement, i.e. external threads on the front sleeve element or rear sleeve element and internal threads on the rear sleeve element or front sleeve element, these being adapted such that they can be screwed together.

The invention claimed is:

1. A syringe device, comprising:
a syringe comprising a front end and a rear end, an axially extending hollow needle that projects from the front end, a rear end of the needle being in fluid communication with a space that extends substantially to the rear end of the syringe, a plunger comprising a piston arranged in the space and a piston rod extending axially from the piston and out of the rear end of the syringe, wherein the piston is movable to and fro in the space, and wherein the plunger is designed such that, when drawn out to a drawn out position, wherein the piston rod extends axially from the rear end of the syringe, the plunger causes liquid to be drawn through the needle and, when pressed in, causes liquid to be discharged through the needle, and a radially projecting grip element configured and dimensioned to be gripped between a thumb and middle finger of a hand of a user while pressing on the piston rod using an index finger of the hand to carry out injection, wherein the grip element has an extent in an axial direction and is circumferentially arranged about a front portion of the syringe, and
a capsule device comprising at least one rear sleeve element which is dimensioned such that, when the plunger of the syringe is drawn out to the drawn out position, the at least one rear sleeve element will cover the piston rod of the syringe such that, when the at least one rear sleeve element is engaged over the piston rod, the plunger cannot be pressed in, wherein the capsule device further comprises at least one front sleeve element designed to cover the needle of the syringe when the syringe is not in use, the grip element of the syringe being designed such that, upon engagement of the at least one front sleeve element, the grip element acts as a limit stop for the at least one front sleeve element, and wherein the grip element of the syringe is designed such that, upon engagement of the at least one rear sleeve element, the grip element acts as a limit stop for the at least one rear sleeve element.

2. The syringe device according to claim 1, further comprising:
a retention element configured to releasably secure at least one of the at least one front sleeve element and the at least one rear sleeve element.

3. The syringe device according to claim 1, wherein at least one of the front sleeve element and the rear sleeve element comprises a fastener configured to attach a key ring.

4. The syringe device according to claim 1, wherein the syringe device includes at least two of the rear sleeve elements connected in parallel to one another to form a rear capsule part.

5. The syringe device according to claim 1, further comprising:
a seal configured to permit liquid-tight enclosure of the syringe by the at least one front sleeve element or the at least one rear sleeve element.

6. The syringe device according to claim 1, wherein the grip element has a substantially oval cross section.

7. The syringe device according to claim 1, wherein the grip element has a substantially circular cross section.

8. The syringe device according to claim 1, wherein the grip element comprises at least two circumferential grip portions arranged substantially parallel to each other.

9. The syringe device according to claim 1, wherein the grip element is flexible.

10. The syringe device according to claim 1, wherein with the piston rod drawn out, the syringe has a length in the range of 30-80 mm.

* * * * *

UNITED STATES PATENT AND TRADEMARK OFFICE
CERTIFICATE OF CORRECTION

Page 1 of 2

PATENT NO. : 8,267,902 B2
APPLICATION NO. : 12/307827
DATED : September 18, 2012
INVENTOR(S) : Patrick Martinsson It is certified that error appears in the above-identified patent and that said Letters Patent is hereby corrected as shown below:

Delete the title page and substitute therefore with the attached title page consisting of the corrected Fig. 1.

In the Drawings

Replace Fig. 1 with the following Fig. 1.

Signed and Sealed this
Eighth Day of April, 2014

Michelle K. Lee
*Deputy Director of the United States Patent and Trademark Office*

CERTIFICATE OF CORRECTION (continued)

(12) United States Patent
Martinsson (10) Patent No.: US 8,267,902 B2
(45) Date of Patent: Sep. 18, 2012

(54) SYRINGE, CAPSULE DEVICE THEREFORE, AND SYRINGE DEVICE

(75) Inventor: Patrick Martinsson, Stockholm (SE)

(73) Assignee: Insulution Svenska AB, Stockholm (SE)

( * ) Notice: Subject to any disclaimer, the term of this patent is extended or adjusted under 35 U.S.C. 154(b) by 269 days.

(21) Appl. No.: 12/307,827

(22) PCT Filed: Jul. 5, 2007

(86) PCT No.: PCT/SE2007/050503
§ 371 (c)(1),
(2), (4) Date: Jan. 7, 2009

(87) PCT Pub. No.: WO2008/004976
PCT Pub. Date: Jan. 10, 2008

(65) Prior Publication Data
US 2009/0312714 A1     Dec. 17, 2009

(30) Foreign Application Priority Data
Jul. 7, 2006   (SE) .................................... 0601499

(51) Int. Cl.
*A61M 5/315* (2006.01)
(52) U.S. Cl. ........ 604/220; 604/192; 604/199; 604/263; 206/364
(58) Field of Classification Search ................. 604/187, 604/192, 197, 198, 199, 227, 263, 220, 218; 206/363, 364, 365, 571
See application file for complete search history.

(56) References Cited

U.S. PATENT DOCUMENTS

| 764,564 A * | 7/1904 | Dreyer ................. 604/192 |
| 2,400,722 A | 5/1946 | Swan |
| 2,473,733 A | 6/1949 | Smith |
| 2,707,466 A | 5/1955 | Hoskins et al. |
| 2,860,635 A | 11/1958 | Wilburn |
| 3,272,322 A | 9/1966 | Ogle |

(Continued)

FOREIGN PATENT DOCUMENTS

GB     1379509     1/1975

(Continued)

OTHER PUBLICATIONS

PCT/ISA/210—International Search Report—Oct. 5, 2007. (3 pages).

(Continued)

*Primary Examiner* — Bhisma Mehta
(74) *Attorney, Agent, or Firm* — Venable LLP; Eric J. Franklin (57) ABSTRACT

A syringe including a front end and a rear end. A front portion of the syringe having an axially extending hollow needle that projects from the front end. The rear end of the needle is in fluid communication with a space that extends substantially to the rear end of the syringe. A plunger extends axially and is movable to and fro in the space and is designed such that, when drawn out, it sucks liquid through the needle and, when pressed in, discharges liquid through the needle. A radially projecting flange element in the front portion of the syringe is designed in such a way that it can be gripped between the thumb and middle finger of a user's hand. The syringe is dimensioned so as to permit injection using the index finger of the same hand. A capsule device for at least partially accommodating a syringe. A syringe device.

10 Claims, 4 Drawing Sheets